United States Patent [19]

Vetter

[11] Patent Number: 4,688,585
[45] Date of Patent: Aug. 25, 1987

[54] AUTOMATIC WASHER, ESPECIALLY FOR CLEANING HANDS AND STERILIZING ARTICLES

[75] Inventor: Helmut Vetter, Ravensburg, Fed. Rep. of Germany

[73] Assignee: Arzneimittel GmbH Apotheker Vetter & Co. Ravensburg, Ravensburg, Fed. Rep. of Germany

[21] Appl. No.: 782,491

[22] Filed: Oct. 1, 1985

[30] Foreign Application Priority Data

Apr. 10, 1985 [EP] European Pat. Off. ........ 85104320.8

[51] Int. Cl.⁴ .............................................. B08B 3/02
[52] U.S. Cl. .................................. 134/56 R; 134/128; 134/200; 118/679
[58] Field of Search ...................... 134/44, 56 R, 57 R, 134/58 R, 113, 172, 175, 177, 123, 199, 200; 604/289; 118/676, 679, 682

[56] References Cited

U.S. PATENT DOCUMENTS 3,038,481  6/1962  Brechtel ........................ 134/123 Y
3,416,544 12/1968  Paina ............................. 134/172 X
3,533,422 10/1970  Alimanestiano ............... 134/57 R
3,691,577  9/1972  Bliss ............................... 134/172 X
3,918,907 11/1975  Kopfer .......................... 134/113 X
4,378,755  4/1983  Magnusson et al. ......... 134/123 X Primary Examiner—Harvey C. Hornsby
Assistant Examiner—Frankie L. Stinson
Attorney, Agent, or Firm—Karl F. Ross; Herbert Dubno

[57] ABSTRACT

An automatic washer for cleaning objects, particularly hands, comprises a housing substantially enclosed on all sides with at least one opening for introduction of the objects to be cleaned, at least one nozzle, preferably a plurality of nozzles, for admitting at least one cleaning medium, whereby the nozzles are aligned and oriented appropriately to clean the surfaces of the object to be cleaned positioned in the interior of the housing, a control device detecting and responding to characteristics, particularly the shape, orientation, and position, of the object inserted into the interior of the housing to be cleaned, so as to activate the cleaning process when those characteristics correspond to those preset in the control device, and an operating mechanism which monitors and controls the method and timely running of the cleaning process.

11 Claims, 4 Drawing Figures

AUTOMATIC WASHER, ESPECIALLY FOR CLEANING HANDS AND STERILIZING ARTICLES

FIELD OF THE INVENTION

My present invention relates to an automatic washer for cleaning various objects and, more particularly, to an automatic washer for cleaning and sterilizing objects especially hands, or to an automatic hand washer for pharmaceutically industrial, medical and other purposes where a high standard of cleanliness is called for.

BACKGROUND OF THE INVENTION

In numerous industrial, e.g., pharmaceutical manufacturing and likewise medical situations, higher cleanliness standards for dust-free and sterile environments are being set. As far as production processes taking place completely in a hermetically sealed clean room there is usually no problem. In contrast bringing objects from a contaminated environment into a clean room is always a critical step, since thereby increased contaminants adhering to the object will be entrained into the clean room. therefore a meticulous and complete cleaning of these objects is required.

That is also true for the work force, whose presence in the clean room is frequently unavoidable. Of course there are special kinds of dust-repellent clothing, for example, by which the introduction of impurities adhering to the clothes is substantially reduced. Cleaning of the hands is however always a problem because rarely are correct cleaning procedures followed; the cleaning process is rushed or is frequently performed incorrectly, whereby dirt bacteria or other microbes are transmitted into clean areas in production, particularly in pharmaceutical production, in hospitals and in food production.

OBJECTS OF THE INVENTION

My invention is based on the recognized need to provide an automatic washer for cleaning of objects, particularly of hands, which automates the cleaning process, so that the cleaning process occurs in a prescribed sequence adapted to the particular conditions. Therefore a resulting state of cleanliness achieved in each case can be monitored and validated.

It is an object of my invention, therefore, to provide an automatic washer for cleaning objects, particularly hands.

It is also an object of my invention to provide an automatic washer for cleaning objects, particularly hands, which meets the high standards of cleanliness required in industrial production, pharmaceutical manufacture, medical and other situations in an accurate and reproducible way.

It is a further object of my invention to provide an automatic washer which reproducibly meets high standards of cleanliness for a variety of different objects and which is programmable so as to be able to recognize each object and to provide the appropriate washing conditions for the appropriate times.

Still another object is to avoid drawbacks of earlier cleaning systems.

SUMMARY OF THE INVENTION

These objects and others which will become apparent hereinafter are attained in accordance with my invention in an automatic washer for cleaning a variety of objects, particularly for cleaning hands.

According to my invention the automatic washer comprises a housing which is essentially enclosed on all sides with at least one opening for the introduction of the objects to be cleaned.

Through one or more nozzles positioned and arranged in the interior of the housing the objects are sprayed with fluid and/or gaseous cleaning media, and the nozzles are suitably oriented and aligned to reach the surfaces of the object to be cleaned or are orientable by the hands of the user in the housing for this purpose.

Furthermore by a control device also positioned inside the housing responding to the shape and position of an object put into the housing, as well as other characteristics such as orientation and the like, the cleaning process is activated, when particular characteristics preset or preprogrammed in the control device are detected, especially the objects' shape, structure, position, or orientation so as to ensure through cleaning of each article and each surface of an article. An operating mechanism controls and monitors the materials and sequences of the cleaning process.

The advantages of my invention include the following: the selection and amounts of the cleaning media applied as well as the sequence and intervals of their application are controlled by a fixed preset program, so that the operator of the apparatus of my invention, that is, the user whose hands are to be cleaned or the one who puts in objects to be cleaned, has no control or influence upon the process and therefore cannot skip a step or terminate the process prematurely.

The cleaning process only runs when the object to be cleaned is located in its position in the housing for optimum cleaning, so that an efficient cleaning of all surfaces of the object can occur.

The operating program can be selected to fit different cleaning requirements for different purposes and situations. Thereby, in summary, reproducibility independent of personal habits and deficiencies and the validation of the cleaning application required in pharmaceutical situations are guaranteed.

In a preferred embodiment of my invention the or each opening in the housing is provided with an elastic sealing member of sleeve attached at its edge to the periphery of the opening. The sealing member acts to seal the object inserted for cleaning. Therefore for the cleaning a complete sealing of the housing is achieved in the vicinity of the openings, whereby no contamination or microbes can make their way into the interior of the automatic washer and on the other hand the cleaning media can not escape to the outside.

In order to achieve a good fit of the sealing member to the objects it is advantageous, when the sealing member has a substantially annular shape being attached to the edge of the opening at its periphery and having a central hole through which the object to be washed is passed in tight sealing relation. Under the force of inserting the object through the central hole into the interior of the automatic washer the sealing member contacts the extended object sealing the housing. Inasmuch as the automatic washer is to be used for washing hands, the sealing member is so constructed to provide a force opposing the insertion force so that an adequate seal is achieved by applying an adjustable air-pressure the forearm is not held so tightly that the hands can not be withdrawn through the sealing member from the apparatus. flow is stopped.

In a preferred embodiment of my invention particularly for cases where ultrahigh or very high cleanliness is required the housing is constructed as a pressure-retentive box and is additionally provided with venting and pressurizing means as well as with a pressure connector for input of pure steam for example. Thus the automatic washer can be operated to frequently provide a sterile heated antimicrobial environment, for example, by flowing in pure steam at 121° C.

The inflating of the box causes the sleeve to hug the forearm and when the pressure is released the hand can be withdrawn.

The housing is formed appropriately from an inert material resistant to all cleaning media such as stain steel. The upper side of the housing can be formed advantageously from a transparent material such as a polyacrylate or polycarbonate, e.g. Macrolon, so that the cleaning process can be observed.

Advantageously the control device can have at least one sensing element, whose contact with the object to be cleaned sends an output signal to a microcomputer or logic circuit, which allows an activating signal to be sent to the operating mechanism controlling the running of the cleaning process. Therefore, when the automatic washer is set up to wash hands, the arrangement of the sensing elements can be so selected that this can occur only when the fingers are spread in a predetermined, correct position. Because of that an effective cleaning between the fingers also occurs. Thus it is also advantageous, when the sensing elements are provided in such number and arrangement, that the presence of several possible orientations of the objects for cleaning which correspond to allowed positions for the cleaning process can be detected.

With the use of sensing elements the cleaning efficiency of opposing contacting surfaces under certain circumstances is limited. Inasmuch as this is undesirable, it is recommended according to a second embodiment of my invention, that the control device should have an electrooptical sensor, which senses the shape of the objects, particularly whether they are linear or flat, and forms an analog image signal to be fed into an analyzer, which by comparison with a preset or preprogrammed image sends an activating signal for operation of the cleaning process to the operating mechanism. Because of that a complete contact-free monitoring of the objects to be cleaned in regard to their shape and orientation is achieved so that the cleaning process can proceed in a way that is not limited to just the upper surface of the objects.

For a particularly compact structure of the automatic washer of our invention storage vessels are included for the cleaning media. Furthermore for selection and application of the various cleaning media activating operational control and adjusting elements (e.g. valves) are provided for the storage vessels and the nozzles. All of these and the mountings holding their associated nozzles are arranged and positioned inside of the automatic washer housing. There is also the possibility however to position at least one supply vessel outside of the automatic washer, whereby storage the cleaning and disinfecting solutions are simplified. Thus one supply vessel can provide a supply of cleaning media for several automatic washers.

Preferably the operating mechanism is provided with a personal identifier in the form of a numeric code-input sensor or a reader for identification cards. This allows programming the unit to respond to the user's identity and also, for example, programming the time and frequency of the cleaning process for that individual user. Subsequently it is also found advantageous, when the operating mechanism provides a valuation or validation signal, which indicates the correct performance of the cleaning process. These valuation signals show, for example, to the user, that the provided cleaning process has run according to plan. Likewise the valuation signal can act as a door control, so that for example, a clean room can be entered only after the planned cleaning process has been completed correctly.

BRIEF DESCRIPTION OF THE DRAWING

The above and other objects, features and advantages of my invention will become more readily apparent from the following description, reference being made to the accompanying drawing in which.

SPECIFIC DESCRIPTION

Figure 1:
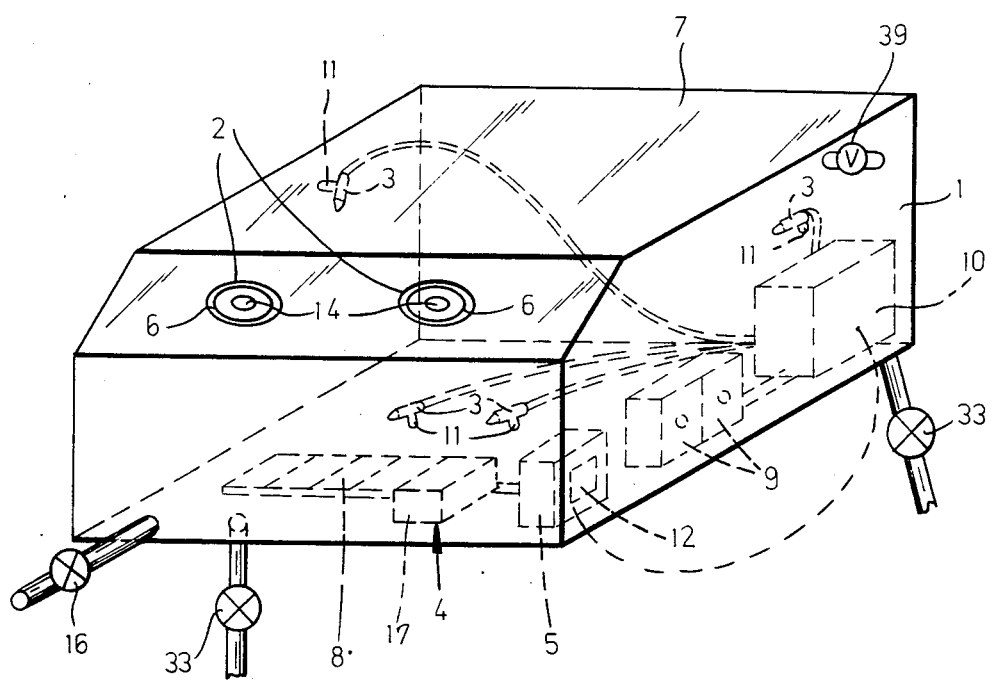
FIG. 1 is a perspective schematic view of a preferred embodiment of an automatic washer according to my invention.

The automatic washer of my invention is commonly used for cleaning various objects, but as shown in FIG. 1 is particularly equipped and constructed for cleaning hands. FIG. 1 shows a housing 1, which essentially encloses all sides of the automatic washer and which is provided with two openings 2, through which the hands to be cleaned are put into the automatic washer. Inside of the automatic washer several nozzles 3 for delivery of fluid and, if necessary, gaseous cleaning media are arranged and appropriately positioned. These nozzles 3 are individually oriented and/or are adjustable within the housing, so that all the surfaces of the object, particularly the hands, to be cleaned are correctly reached.

In the interior of the housing 1 a control device 4 is positioned, which responds to the shape and the position of the object to be cleaned in the housing 1. In so far as they correspond with the position and shape of the object which is supposed to be cleaned, the cleaning processes are activated by an operating mechanism 5, which usually also controls and monitors the operation and/or timely running of the cleaning process.

Figure 3:
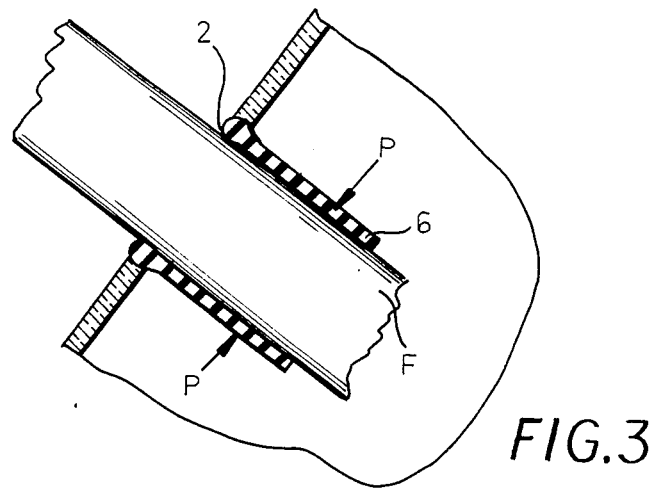
FIG. 3 is a detail section showing a sealing sleeve.

Each of the openings 2 is provided with an elastic sealing member or sleeve 6 attached to its edges for sealing the objects to be cleaned (See also FIG. 3). This sleeve prevents cleaning fluid media from the inside of the housing 1 from reaching the outside. Likewise the entry of dust and bacteria into the housing 1 during cleaning is prevented. Furthermore the elastic sealing member 6 has as can be seen in FIG. 3 an annular shape, running substantially on the periphery of the opening and structured for sealing on the object to be cleaned which is forced in the central hole 14. In this way an easy insertion of the object into the automatic washer is possible, since the elastic sealing member 6 is constructed to seal itself to it at the beginning of the cleaning process. When pressured air is applied the pressure acts on the sleeve (arrows) to press it against the forearm F.

The housing 1 in a way likewise not shown in FIG. 1 is constructed as a pressure box, in order to allow occasionally a sterilization of the interior, for example by introducing steam with a temperature of 121° C. Additionally the housing 1 is provided with a pressure connector 16 for input of the pure steam. The housing 1 comprises an inert material resistant and nonreactive to the cleaning media such as stainless steel, wherein only the upper side 7 of the housing 1 is constructed of a transparent material for observation of the cleaning process, for example a transparent material such as Macrolon.

The control device 4 has an electrooptical sensor 8, which senses which object is in the housing 1 for cleaning according to its shape, for example according to whether it is linear or flat. The structural image information ascertained from the electrooptical sensor 8 is transmitted into an analyzer 17, which when that type of image has been stored and is preset, sends the activation signal for operation of the cleaning process to the operating mechanism 5. These kind of control devices based on optical principles are known, for example as described in German Patent DE-PS No. 26 38 138, in which one such control device 4 for detecting and sorting out defective packagings is described.

Figure 2:
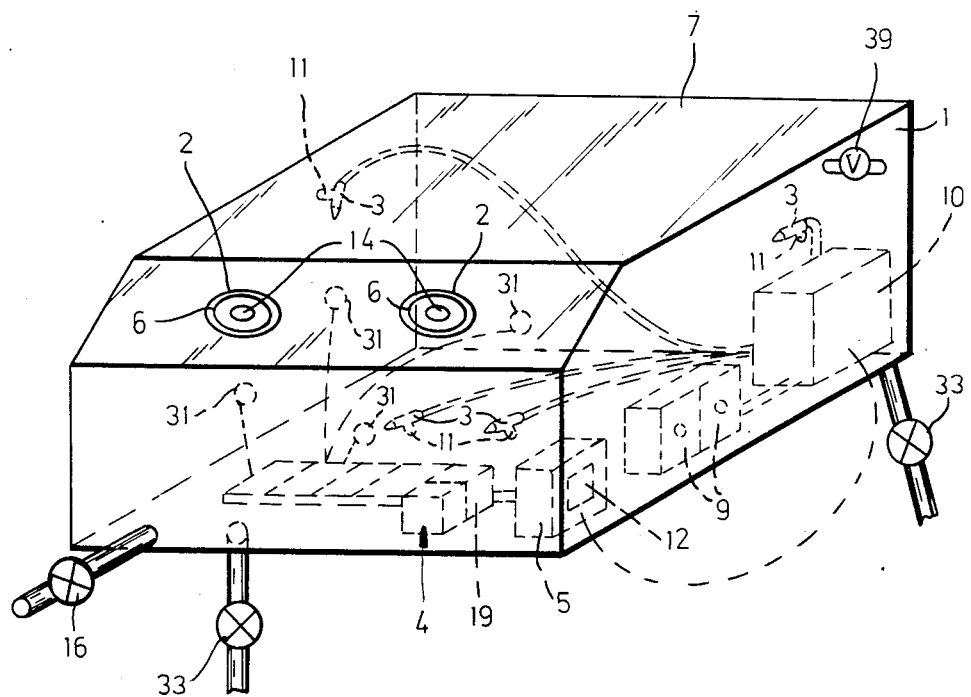
FIG. 2 is a perspective schematic view of another embodiment of an automatic washer according to my invention.

In a simpler specific embodiment the control device 4 in a way shown in FIG. 2 has sensing elements 31, which produce an output signal when in contact with the objects which the apparatus is to clean. These output signals can be fed into a computer 19, which again sends an activation signal to the operating mechanism 5 for operation of the cleaning process when an appropriately related preset form and/or shape is present in the computer 19. In an automatic washer for cleaning hands the control device 4 is so adjusted that an activation of the washing process then results, when the individual fingers are spread apart, so that the space between the fingers are also subject to the cleaning.

In the compact form of th automatic washer shown in FIGS. 1 and 2 supply vessels 9 for containing the various cleaning and disinfecting solutions are located. Operational control and adjusting elements 10 for the selection and use of the different cleaning media are put in and appropriately positioned as well as metering pumps, valves and the like and subsequently also the supply vessels 9 with the operational control and adjusting elements 10 and the mountings 11 with the nozzles 3 are positioned appropriately in the interior of the housing 1. However it is also possible to connect several such washers to a central supply vessel 9, which permits a simpler filling of the cleaning and disinfecting solution.

Subsequently the operating mechanism 5 is provided with a personnel identifier in the form of a reader 12 for identification cards, which is a part of the operating mechanism 5. That allows for example the control and determination of the sequence and intervals of the washing process for each individual case. Therefore the operating mechanism 5 can also make an analyzer signal, which can serve as a receipt of an order or ranking for running the washing process. The analyzer signal can however also be used to control the access to a clean room in this manner, so that the door to the clean room is only opened after running the cleaning process as described.

The automatic washer can usually be adjusted, so that a drying process can be set up in connection to the cleaning, in which sterile air is blown into the inside of the housing 1 by the nozzles 3.

The operating mechanism 5 is suitably advantageously completely programmable in regard to the sequence and intervals of running the cleaning process. Thus the following cleaning procedure can be given:

After identification of the personnel the elastic sealing member 6 allows entry into the apparatus. In the presence of the appropriate preset shape and form of the object, the sleeve is inflated and then the cleaning process is activated. After a short wetting of the objects (hands) the principal cleaning process occurs, subsequent to which a rinsing with water and a drying with sterile air take place. After a spraying with disinfectant solution and after a recording of the newly achieved status for quantitative evaluation of the cleanliness, the opening of vent valve 39 controlling the pressure on the elastic sealing member 6 occurs allowing removal of the object to be cleaned or the hand, and, if necessary, subsequent release of sluice as well as opening of the water outlet valves 33 occurs also.

Figure 4:
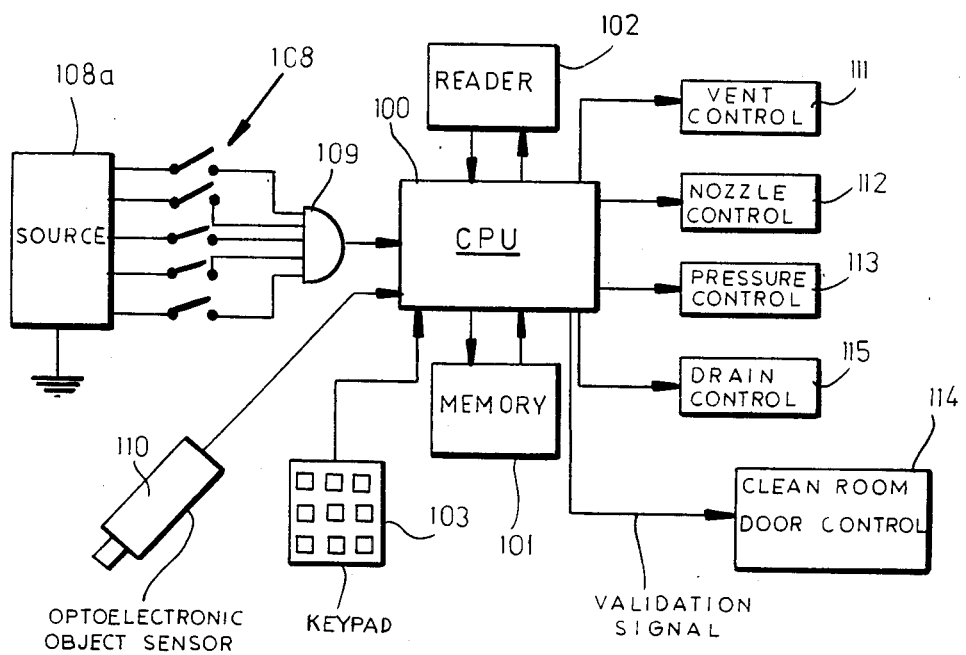
FIG. 4 is a block diagram of the circuit of the invention.

The control circuit is represented in FIG. 4 wherein the microcomputer previously described is represented at 100 and is connected with the usual RAM memory 101 which can be preprogrammed to establish washing cycles for various objects or users. The user or objects can be identified by a card read by the reader 102, or inputted as a code by the keypad 103. The proper positioning of the objects may be detected by the simultaneous closing of switches 108 of the optoelectronic unit connected to the current source 108a. The logic circuitry is represented by the AND-gate 109. Another optoelectronic unit which can be used is an image producing unit 110 (e.g. a video camera) which inputs an image signal to the CPU 100. The latter in accordance with the memory operates the venting valve controller 111, the nozzle valve controller 112, the drain valve controller 115, and the pressure valve controller 113 and, when the process is complete, operating the clean room door control 114.

I claim:

1. An automatic washer for the reproducible washing of hands and other articles and for preventing the contamination of a surrounding space, said washer comprising:
    a box-like housing defining a washing chamber sealed from said surrounding space and formed with at least one wall provided with at least one opening receiving a flexible seal through which a hand to be washed can be inserted;
    nozzle means including at least one nozzle orientable in said housing to train a jet of at least one cleaning medium upon an object disposed in said chamber and which can be a hand introduced through said opening;
    program-storage means provided with preprogrammed parameters of cleaning processes including:
        washing, rinsing and drying fluids constituting respective cleaning media to be discharged by said nozzle means,
        patterns of distribution of said cleaning media onto and over objects of various orientations, configurations and types adapted to be disposed in said chamber,
        amounts of said cleaning media to be discharged by said nozzle means onto and over objects of various orientations, configurations and types adapted to be disposed in said chamber, and duration of discharge of said cleaning media by said nozzle means onto and over objects of various orientations, configurations and types adapted to be disposed in said chamber for cleaning and decontamination thereof;

means for detecting and responding to the shape, orientation and position of an object introduced into said chamber and connected to said program-storage means for effecting washing of said object introduced into said chamber in accordance with selected ones of said parameters of cleaning media and of patterns of distribution, amounts of cleaning media and duration of discharge in accordance with the detected shape, orientation and position to ensure complete cleaning of said object introduced into said chamber; and means for signalling the completion of a program of washing in accordance with said selected ones of said parameters.

2. The automatic washer defined in claim 1 wherein said flexible seal provided in said opening is an elastic sealing member which is annular and fastened onto each of said openings, said sealing member having a central hole adapted to engage sealingly around the arm of a user.

3. The automatic washer defined in claim 1 wherein said housing is a pressure box and is provided with means for pressurizing the interior of said box.

4. The automatic washer defined in claim 1 wherein said housing is composed of stainless steel and has a transparent top.

5. The automatic washer defined in claim 1 wherein said means for detecting comprises a plurality of sensing elements fixed in said housing and provided in such number and arrangement that a variety of orientations of the object to be cleaned can be detected.

6. The automatic washer defined in claim 1 wherein said means for detecting includes an electrooptical sensor which senses the shape of the object introduced into said chamber, an image analyzer receiving an image signal from said sensor and means for comparing a preset image to said image signal for activating a cleaning operating under the control of said program-storage means when said preset image corresponds to said image signal.

7. The automatic washer defined in claim 1 wherein said means for detecting includes a personnel identifier.

8. The automatic washer defined in claim 7 wherein said personnel identifier is a numeric code input sensor for identification cards.

9. The automatic washer defined in claim 7 wherein said personnel identifier is a card reader for an identification card.

10. The automatic washer defined in claim 1 wherein said automatic washer is contained in a clean room provided with a door, further comprising means for unlocking said door in response to a signal from signaling means.

11. An automatic washer for the reproducible washing of hands and other articles and for preventing the contamination of a surrounding space, said washer comprising:

a box-like housing defining a washing chamber sealed from said surrounding space and formed with at least one wall provided with at least one opening receiving a flexible seal through which a hand to be washed can be inserted;

nozzle means including at least one nozzle orientable in said housing to train a jet of at least one cleaning medium upon an object disposed in said chamber and which can be a hand introduced through said opening;

program-storage means provided with preprogrammed parameters of cleaning processes including:

washing, rinsing and drying fluids constituting respective cleaning media to be discharged by said nozzle means, patterns of distribution of said cleaning media onto and over objects of various orientations, configurations and types adapted to be disposed in said chamber, amounts of said cleaning media to be discharged by said nozzle means onto and over objects of various orientations, configurations and types adapted to be disposed in said chamber, and duration of discharge of said cleaning media by said nozzle means onto and over objects of various orientations, configurations and types adapted to be disposed in said chamber for cleaning and decontamination thereof; and means for detecting and responding to the shape, orientation and position of an object introduced into said chamber and connected to said program-storage means for effecting washing of said object introduced into said chamber in accordance with selected ones of said parameters of cleaning media and of patterns of distribution, amounts of cleaning media and duration of discharge in accordance with the detected shape, orientation and position to ensure complete cleaning of said object introduced into said chamber.

* * * * *